(12) United States Patent
Murray et al.

(10) Patent No.: US 8,337,019 B2
(45) Date of Patent: Dec. 25, 2012

(54) TESTING VISION

(75) Inventors: Ian Murray, Edinburgh (GB); Robert Minns, Edinburgh (GB); Brian Fleck, Edinburgh (GB); Harry Brash, Edinburgh (GB)

(73) Assignee: University Court of the University of Edinburgh, Edinburgh (GB)

( * ) Notice: Subject to any disclaimer, the term of this patent is extended or adjusted under 35 U.S.C. 154(b) by 295 days.

(21) Appl. No.: 12/600,419

(22) PCT Filed: Apr. 25, 2008

(86) PCT No.: PCT/GB2008/001480
§ 371 (c)(1),
(2), (4) Date: Mar. 30, 2010

(87) PCT Pub. No.: WO2008/139137
PCT Pub. Date: Nov. 20, 2008

(65) Prior Publication Data
US 2010/0195051 A1 Aug. 5, 2010

(30) Foreign Application Priority Data
May 16, 2007 (GB) .................................. 0709405.5

(51) Int. Cl.
*A61B 3/14* (2006.01)
(52) U.S. Cl. ......................................... 351/209; 351/208
(58) Field of Classification Search ........... 351/200–246
See application file for complete search history.

(56) References Cited

U.S. PATENT DOCUMENTS

| | | | |
|---|---|---|---|
| 5,459,536 A | 10/1995 | Shalon et al. | |
| 5,920,375 A | 7/1999 | Fahle et al. | |
| 6,129,722 A * | 10/2000 | Ruiz | 606/5 |
| 6,290,357 B1 * | 9/2001 | Massengill et al. | 351/209 |
| 2006/0114414 A1 * | 6/2006 | McGrath et al. | 351/246 |

FOREIGN PATENT DOCUMENTS

| | | |
|---|---|---|
| DE | 195 05 399 A1 | 8/1996 |
| EP | 1 397 991 A1 | 3/2004 |
| GB | 2 096 791 A | 10/1982 |
| GB | 2375821 A | 11/2002 |
| WO | WO 99/22638 | 5/1999 |
| WO | WO 2004/045399 A1 | 6/2004 |
| WO | WO 2006/029048 A2 | 3/2006 |
| WO | WO 2006/106877 A1 | 10/2006 |
| WO | WO 2008/106802 A1 | 9/2008 |

OTHER PUBLICATIONS

International Search Report for corresponding PCT/GB2008/001480; completed Aug. 6, 2008 by Carlos Rivera Pons of the EPO.

(Continued)

*Primary Examiner* — Mohammed Hasan (57) ABSTRACT

A system for testing visual fields comprising a display for presenting a visual stimulus and an eye tracker for tracking movement of at least one of a patient's eyes to determine its position in three dimensions without requiring the patient to wear any tracking equipment. A computer controls the position of the stimulus on the display and causes it to move by an amount that is a function of the tracked three-dimensional position of the patient's eye and a visual field position that is to be tested. Changes to the position of the stimulus and any corresponding tracked eye movement are used to assess the patient's visual field.

24 Claims, 6 Drawing Sheets

OTHER PUBLICATIONS

Quinn, et al.: "*Visual Fields in 4- to 10-Year-Old Children Using Goldmann and Double-Arc Perimeters*"; Journal of Pediatric Ophthalmology and Strabismus; 1991, vol. 28, Pt. 6, pp. 314-319.

Nunokawa, et al.: "*The Influence of Fixation on New Visual Field Measurement Using Saccadic Eye Movement*"; International Congress Series; 2005, vol. 1282, pp. 674-678.

Safran, et al.: "*Feasibility of Automated Visual Field Examination in Children Between 5 and 8 Years of Age*"; British Journal of Ophthalmology; 1996, vol. 80, Pt. 6, pp. 515-518.

Ideguchi, et al.: "*Development of an Objective Automatic Perimetry Using Saccadic Eye Movement*"; International Congress Series; 2005, vol. 1282, pp. 585-589.

Tschopp, et al.: "*Automated Visual Field Examination in Children Aged 5-8 Years, Part I: Experimental Validation of a Testing Procedure*"; Vision Research; 1998, vol. 38, Pt. 14, pp. 2203-2210.

Search Report for corresponding GB0709405.5, dated Jul. 26, 2007.

Balachandran, et al.: "*Multifocal VEP in Children: Its Maturation and Clinical Application*"; Br. J. Ophthalmol. 2004; 88; 226-232 doi: 10.1136/bjo.2003.018390; downloaded from bjo.bmj.com on Mar. 5, 2007.

http://www.tobii.com/products_-_services/oem_integration_eye_tracking_components/ , Jul. 25, 2007; "*OEM Integration Eye Tracking Components*".

Tobii technology; Tobii 50 Series; www.tobii.com , 2003-2005, pp. 1-15.

\* cited by examiner

TESTING VISION

The present invention relates to a system and method for testing vision, for example visual fields. The invention is particularly suited to testing visual fields in children.

BACKGROUND OF THE INVENTION

The detection of visual field defects is crucial in the management of children with cerebral visual impairment, cerebral tumour and raised intracranial pressure. There is also call for a reliable and sensitive method to monitor visual field changes in children who are taking Vigabatrin for epilepsy. Unfortunately, most existing methods of perimetry are not suitable for children. Children have different needs and requirements to adults when it comes to perimetry, because of their reduced ability to learn tasks and to provide appropriate responses during conventional testing. Children are also less inclined to cooperate due to a lack of understanding of the test methods and their short attention span.

In adults, the reliability of most standard visual field testing methods is dependent upon the ability of the subject to learn the task asked of them during the test. The two main tasks are to fixate on a central target and to indicate by, for example, pressing a button when they see a light stimulus in their field of vision. In order to keep a continuous fixation on a central target when a stimulus is presented in their visual field, the subject needs conscious effort to inhibit their natural response to fixate on the stimulus, thereby preventing the loss of fixation on the central target. It is much more difficult for children, especially children below the age of five to inhibit the natural saccadic reaction that is triggered by light stimuli in the visual field.

Recognising such difficulties, various groups have looked for better methods of perimetry in children. Methods of perimetry can be loosely divided into kinetic and static perimetry. Among the more popular methods used with children is kinetic and double-arc perimetry, as described by Quinn G E, Fea A M, Minguini N. "Visual fields in 4- to 10-year-old children using Goldmann and double-arc perimeters." J. Pediatr. Ophthalmol. Strabismus 1991 November-December; 28(6): 314-319. Kinetic perimetry gives some control and freedom to the examiner, thus conferring the advantage of adaptability to the child's age and maturity. However, a disadvantage is the need for the child's cooperation in maintaining a continuous fixation on a central target during the test. Another disadvantage is that results of the test are dependent upon the examiner's skills and knowledge, which means that they cannot be used to provide quantitative data for serial comparison studies. Automated static perimetry (ASP) using perimeters such as the Humphrey Visual Field Analyzer, on the other hand, allows for measurement of quantitative data that can be used for serial comparison. However, a continuous central target fixation is still required of the child.

Two groups have modified the ASP test using the Octopus 2000R perimeter in attempts to make it more suitable for children. As described in the article "Feasibility of automated visual field examination in children between five and eight years of age". Br. J. Ophthalmol. 1996 June; 80(6): 515-518, Safran et al used a specially designed programme conducted for progressive familiarisation and a custom "two-level" strategy. The mean test duration was thirteen minutes per eye for five year-olds and seven minutes for eight year-olds. It was found that such strategy was suitable for children age eight and above. For children age seven and below, a preliminary familiarisation phase is mandatory. "Automated visual field examination in children aged five to eight years. Part I: Experimental validation of a testing procedure." Vision Res. 1998 July; 38(14): 2203-2210 describes a meticulous four or five phase procedure with test trials to be used with customised software strategies and a perimeter using a "little bear" as the central fixation target. It was found that such a method is suitable for children age six and above. Whilst both of these methods have the advantage of catch trials for detection of false-positive and false-negative responses, the lengthy and meticulous training and familiarisation phases used may not be practical for usage in a busy clinical setting.

In recent years, new methods of perimetry that use a personal computer with LCD screens have been used in children: for example, Rarebit perimetry and High Pass Resolution (HPR) Perimetry. The Rarebit perimetry uses a dynamic and moving fixation target, which enhances fixation. Subjects were asked to respond by single or double mouse-clicks depending upon the number of perceived dots in the moving fixation target. This is a dynamic test as the pace can be adapted to the reaction time of the subject, thus allowing them to feel more in control of the whole process. The test duration can be varied according to the type of information needed and ranges from less than 1 minute to 5 minutes. The Rarebit perimetry is popular amongst the children as it mimics a computer game. Another advantage is that it does not require the use of a headrest or a bowl, which is appealing to children. One of the disadvantages of Rarebit perimetry is the high false positive response rate, which reduces its reliability. Moreover, subjects need to possess fairly sophisticated motor skills to respond appropriately.

High Pass Resolution (HPR) perimetry uses a personal computer, a monitor and ring-shaped high pass spatial frequency filtered targets of different sizes. Like Rarebit perimetry, this has been popular as it appears like a pleasant game to the children. The test duration is five minutes and was found to be suitable for children age five and above. HPR perimetry, like Rarebit perimetry, does not use a headrest and adapts the pace of the test to the current reaction time of the subject. However, a disadvantage of HPR is the need for a continuous fixation on a central target during the test.

All the methods of perimetry described above depend upon subjective patient responses. An objective method of measuring visual field is the multifocal-Visual Evoked Potential (m-VEP). This involves placing electrodes on the scalp and recording electrical activity from the occipital cortex following presentation of light or pattern stimulus to the retina. This needs minimum cooperation from the subject, and thus is highly suitable for use with children. The test duration for one eye is four minutes for m-VEP. However, M-VEP has inherent disadvantages. There is inter-individual anatomical variation of occipital cortex folding making cortical mapping of visual field responses almost impossible to calibrate. The subject also needs to maintain a continuous fixation on a central target during the test. More importantly for children, the subjects' movements are restrained during the test with bipolar occipital inion straddle electrodes. Not all children can tolerate such devices.

ASP is the visual field assessment method of choice in adults. However, it is rarely reliable in children under nine years of age. Research efforts to perform ASP in children have concentrated on studying the feasibility of using current adult perimetry techniques with children. Following the development of algorithms designed to provide faster testing time such as SITA Fast and TOP, investigations into using these techniques with children were made. However, the youngest age able to produce reliable results is still only in the region of seven to eight years. Training and familiarisation strategies for particular techniques have been looked at as a route to improving reliability, which has shown some success. However, this still does not address the fundamental problems inherent in performing ASP on children.

U.S. Pat. No. 5,459,536 describes an automated perimetry system, in which a patient's visual field can be tested. This requires that the patient's head be restrained in a very restricted position. U.S. Pat. No. 4,059,348 describes another visual field testing system, but again the patient's head has to be held in a fixed position. In both cases, the requirement for the patient's head movement to be severely restricted makes these systems unsuitable for use with young children.

Nunokawa et al have proposed a perimetry method that uses saccadic eye movement as an index, see "Development of an Objective Automatic Perimetry Using Saccadic Eye Movement", International Congress Series 1282 (2005) 585-589, and "The Influence of Fixation on New Visual Field Measurement Using Saccadic Eye Movement", International Congress Series 1282 (2005) 674-687. This method involves presenting a visual stimulus to a user and tracking the movement of a patient's eye in response to that stimulus. The eye tracking is done using an Eyetracker Toolbox provided by Cambridge Research Systems. This has a video eye tracker module that is mounted on a rigid EyeLock™ headrest. In use, a patient has to place their head on the headrest so that the eye tracker can track eye movement. Whilst using the movement of a patient's eye to measure perimetry has significant advantages, the requirement for restricted head movement can be problematic when children or people with learning disabilities are involved.

GB 2,096,791 describes a system for determining visual field in which the patient has to wear a head-mounted helmet that has an integral screen. Various shapes are shown at different positions on the screen, which is a fixed distance from the patient's eyes, so that the patient's visual field can be tested. WO 99/22638 describes a system for testing a patient's visual field by tracking eye movements using goggles that are connected to an eye tracking system. Whilst in these systems, the patient is allowed some degree of head movement the requirement for a patient to wear some form of measurement equipment on their head can be problematic when children or people with learning disabilities are involved.

SUMMARY OF THE INVENTION

According to one aspect of the present invention, there is provided a system for testing visual field comprising: a display for presenting a visual stimulus; an eye tracker for tracking movement of at least one of a patient's eyes to determine a gaze point and its position in three dimensions without requiring the patient to wear any tracking equipment; means for changing the position of the stimulus on the display by an amount that is a function of the tracked three dimensional position of the patient's eye and a visual field position that is to be tested, and means for using the change to the position of the stimulus and any tracked eye movement in response to the change of the position to assess the patient's visual field.

Using an eye tracker arrangement that can track eye movement over a wide range of head positions without requiring a patient to wear eye-tracking equipment allows a patient freedom to move. At the same time, by tracking the 3D position of a patient's eye, test accuracy can be ensured. Hence, patient comfort and so compliance with the test can be significantly improved, whilst ensuring a high level of test reliability. This is essential for testing visual field for young children. Testing visual fields is very useful as it can provide an early indication of various conditions, for example glaucoma.

The system may further comprise means for varying the size of the stimulus presented, as a function of three-dimensional position of the patient's eye and a visual field position that is to be tested, so that stimuli are presented at a constant angular size.

The system may further comprise means for varying the shape of the stimulus presented, as a function of three-dimensional position of the patient's eye relative to the display screen and a visual field position that is to be tested, so that stimuli are presented at a constant angular shape.

Preferably, the eye tracker has a minimum head position tolerance of 10 cm×10 cm×10 cm, for example 20 cm×10 cm×20 cm (Horizontal×Vertical×Distance from the tracker).

Preferably, the eye tracker provides data for the calculation of the 3-dimensional position in space of each eye relative to the eye tracker.

Preferably, the eye tracker includes or consists of the Integration Eye Tracking Component provided by Tobii Technology.

The system may be adapted to present a first stimulus; capture gaze data for that first stimulus; present a second stimulus, and test whether the patient has seen that second stimulus.

The test of determining whether a patient has seen the second stimulus may involve comparing the direction in which the patient's eye(s) moved with the vector direction associated with a line between the first stimulus and the second stimulus. In the event that the direction is substantially the same or the same within pre-determined limits, it is assumed that the patient could be looking at the second stimulus. In this case, the test may further involve comparing the angular distance between the first fixation point and the second fixation point and the angular distance between the first and second stimuli. In the event that these distances are the same or the same within pre-determined limits, it is assumed that the patient is looking at the second stimuli.

The system may be operable to measure at least one of visual acuity, colour vision, contrast sensitivity and colour-contrast sensitivity. To this end, means may be provided for varying the separation of two stimuli for testing visual acuity and/or the colour of the stimulus presented for testing colour and/or contrast of the stimulus for testing contrast sensitivity.

According to yet another aspect of the invention, there is provided a computer program or computer program product preferably on a data carrier or computer readable medium or a processor comprising code or instructions for presenting a visual stimulus on a display; receiving data from an eye tracker on the three dimensional position of a patient's eye(s); changing the position of the stimulus on the display by an amount that is a function of the tracked three dimensional position of the patient's eye and a visual field position that is to be tested, displayed at a size which is a function of the tracked three dimensional position and predetermined angular size, and using the change to the position of the stimulus and any tracked eye movement in response to the change of the position to assess the patient's visual field.

The program/product/processor may be adapted to relocate the position of the stimulus on the screen and use eye-tracking information to determine whether the patient is looking at the stimulus at its new position.

The program/product/processor may be adapted to present a first stimulus; capture gaze data for that first stimulus; present a second stimulus, and test whether the patient has seen that second stimulus.

Determining whether a patient has seen the second stimulus may involve using eye tracking information to compare the direction in which the patient's eye(s) moved with the vector direction associated with a line between the first stimulus and the second stimulus. In the event that the direction is substantially the same or the same within pre-determined limits, the test further involves comparing the distance between the first fixation point and the second fixation point and the distance between the first and second stimuli. In the event that these distances are the same or the same within pre-determined limits, it is determined that the patient is looking at the second stimuli.

The program/product/processor may be arranged to determine a time between showing a first stimulus, deleting that stimulus and displaying a second stimulus and the time for a patient to respond to the change in stimulus. This time information can then be used to identify, at least in part, whether the patient is responding to the stimulus.

According to another aspect of the invention, there is provided a system for testing visual fields comprising: a display for presenting a visual stimulus; an eye tracker for tracking movement of at least one of a patient's eyes to determine its position in three dimensions without requiring the patient to wear any tracking equipment; means for changing the position of the stimulus on the display; means for determining the visual field position associated with the new position of the stimulus using its position on the display and the three dimensional position of the patient's eye(s), and means for using the change to the position of the stimulus, the determined visual field position and any tracked eye movement in response to the change of the position to assess the patient's visual field.

According to still another aspect of the present invention, there is provided a system for testing vision, the system comprising a display for presenting a visual stimulus; means for causing a change to the stimulus; an eye tracker for tracking movement of a patient's eye and means for monitoring the change to the stimulus and any corresponding tracked eye movement to assess the patient's vision, wherein the means for causing a change to the visual stimulus are operable to vary separately or simultaneously two or more of the position of the stimulus; the colour of the stimulus; the contrast of the stimulus. In this way, there is provided a simple and effective system for conducting multiple different types of eye tests.

Two or more stimuli may be presented and the means for causing a change may be operable to vary the separation of the stimuli, thereby to allow visual acuity to be measured.

BRIEF DESCRIPTION OF THE DRAWINGS

Various aspects of the invention will now be described by way of example only and with reference to the accompanying drawings, of which.

SPECIFIC DESCRIPTION OF THE DRAWINGS

Figure 1:
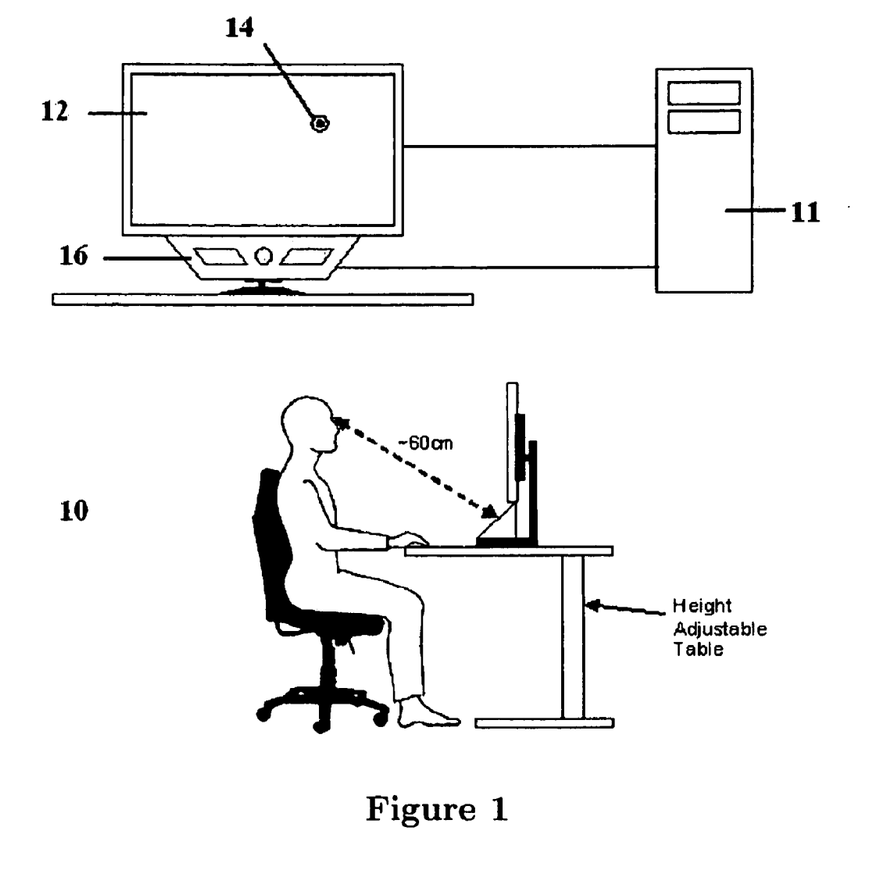
FIG. 1 is a schematic diagram of a system for measuring visual fields.

FIG. 1 shows a system 10 for measuring peripheral vision. This has a personal computer that has a processor 11 with a screen 12 for presenting a visual stimulus 14, typically a circular stimulus, and an eye tracking system 16 for tracking saccadic eye movement when the stimulus 14 is presented in the periphery of a patient's visual field. Included in the processor is software for controlling the presentation of the stimulus on the screen and using the known position of this and information from the eye tracking module to determine whether a patient is looking at a stimulus or not. The only task required of the patient, typically a child, is to follow his natural reaction to fixate on the stimulus 14 of interest when he sees it. By monitoring saccadic eye movements, the system is able to detect changes in eye gaze position. The vector of the saccadic eye gaze movements indicates whether the patient perceives the stimulus 14 or not. The time interval between presentation of the stimulus 14 and the child's response can also be used to confirm that the eye saccadic movements are a reaction to the peripheral stimulus 14 presented.

Any suitable eye tracking system could be used, provided it is able to track eye movement over a wide range of head positions, ideally with a range of 20×10×20 cm, and able to provide data for calculation of the 3-dimensional position in space of each eye relative to the eye tracker, whilst not requiring the patient to wear any form of head mounted equipment or to have a fixed head position. In a preferred example, the eye tracking system provided by Tobii is used. This has a head position tolerance of 30×15×20 cm and is able to detect the distance of a child's eyes from the eye tracker and the position of the eyes in the camera field of view, thereby allowing for the calculation of the three dimensional position of the eyes from a current fixation point. This is essential for calculating where stimuli are to be displayed for assessing any particular visual field angle. The device does not need positional calibration, so the child is free to move around within the field of detection. Also, it provides good gaze data accuracy and the ability to detect the very fast movements of the eye in real time and does not require the subject to wear any equipment on their head. This allows freedom of head movements, which is a clear benefit for children. Also, the eye tracker has no moving parts and as such is highly unobtrusive, which is of importance as children can be easily distracted.

In order to allow the calculation of the appropriate screen position for any particular visual field point being assessed, the position of each eye in 3-dimensional space relative to the display screen must be known. The Tobii eye tracker provides real time data giving the distance of each eye from the eye tracker camera and the position of each eye in the camera field of view. This allows the real time calculation of the 3D position of each eye relative to any point on the display screen and so provides a way of determining the correct size and position of the stimuli to be presented on the screen at any moment and for any particular visual field point being assessed.

Figure 2:
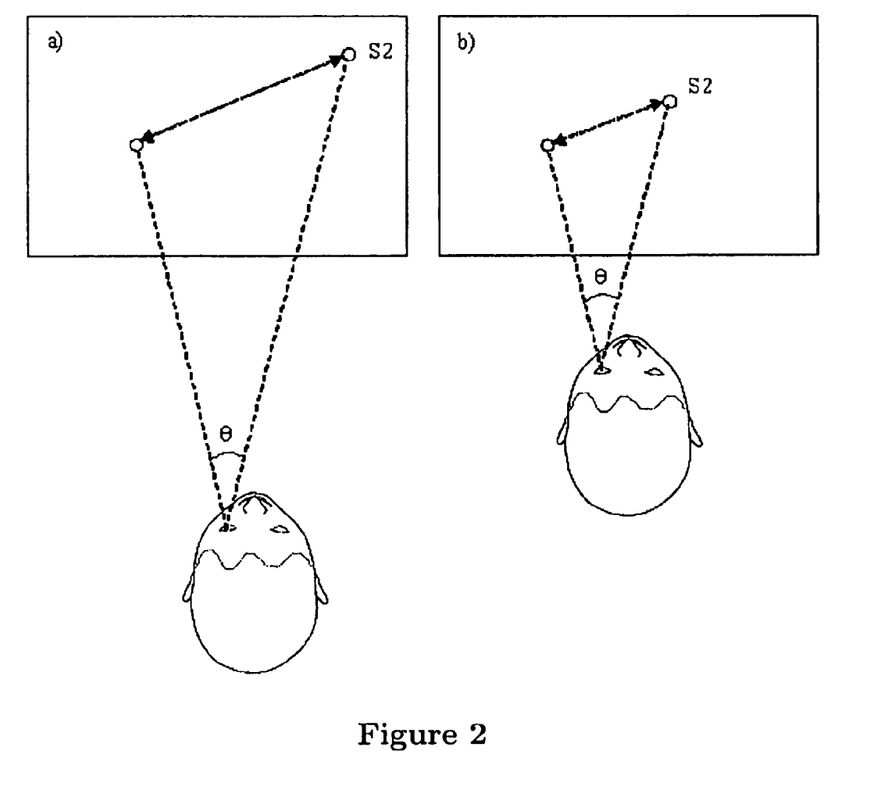
FIG. 2 illustrates the effect of distance from a test screen on the location of the stimulus that is presented.

FIG. 2 demonstrates how the screen position for a visual field point being assessed is dependant upon the 3D position of the subject's eyes relative to the display. This shows two examples (a) and (b) that allow testing of the patient's visual field at angle ~ In each case, remains unchanged, but the position of the second stimulus (S2) changes as a function of the position of the patient's eyes relative to the screen. Hence, to ensure that there is an accurate measure of the patient's vision at a particular angle, the 3D position in space of each eye has to be carefully monitored, so that the stimulus can be positioned and correctly associated with the particular visual field point being assessed.

Figure 3:
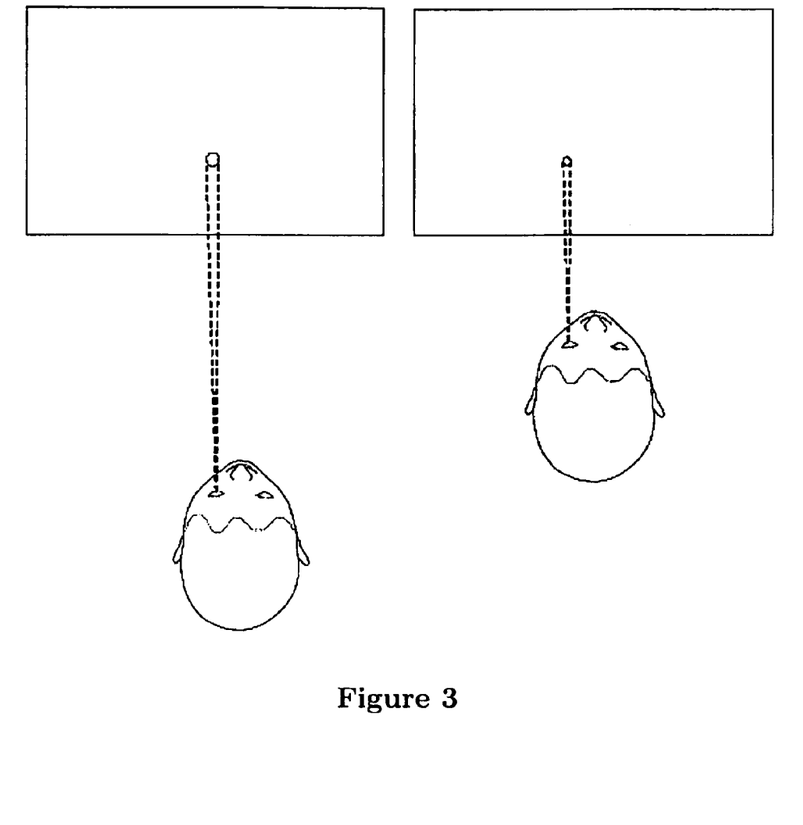
FIG. 3 illustrates the effect of distance from a test screen on the size of the stimulus that is presented.

As well as varying the position of the stimuli as a function of the position of the patient's eye, the actual size of the stimuli being displayed on the screen also has to be varied dependant upon the distance the subject's eyes are away from the screen. This is because the angular stimulus size must be kept constant for all visual field points during a test. Hence, the size is also varied depending on the location of the patient's eyes, as shown in FIG. 3.

Optionally, the system may also be adapted to take into account the fact that the stimuli displayed to test visual field points may not be directly in front of the patient and so to this end, the system may vary the shape of the stimulus presented, as a function of three-dimensional position of the patient's eye relative to the display screen and the visual field position that is to be tested, so that stimuli are presented at a constant angular shape. For example, where the test stimulus is circular and the display screen is flat, in the event that the stimulus is not directly in front of the patient, the shape presented on screen may in fact be elliptical, so that when viewed from an angle, is it perceived as being circular.

The response of a subject's eye gaze is monitored when stimuli 14 are shown in different positions on the display screen 12 corresponding to different points in a subject's visual field. An algorithm is used to decide whether the subject was able to see the new stimulus based on the direction and length of movement of eye gaze and the timing of that movement. If a subject sees something in their peripheral vision the natural response is to gaze at it. If the point is not seen there could be no change in eye gaze position or a searching eye gaze movement. The algorithm automatically distinguishes these responses in real time based on the direction and angular length of any fixation change made immediately following the presentation of a new visual field point stimulus, and the timing of any such fixation change. The vector change in fixation point is compared directly with the vector change in the screen position of the stimuli to decide if the subject was able to see the stimuli or not.

Figure 4:
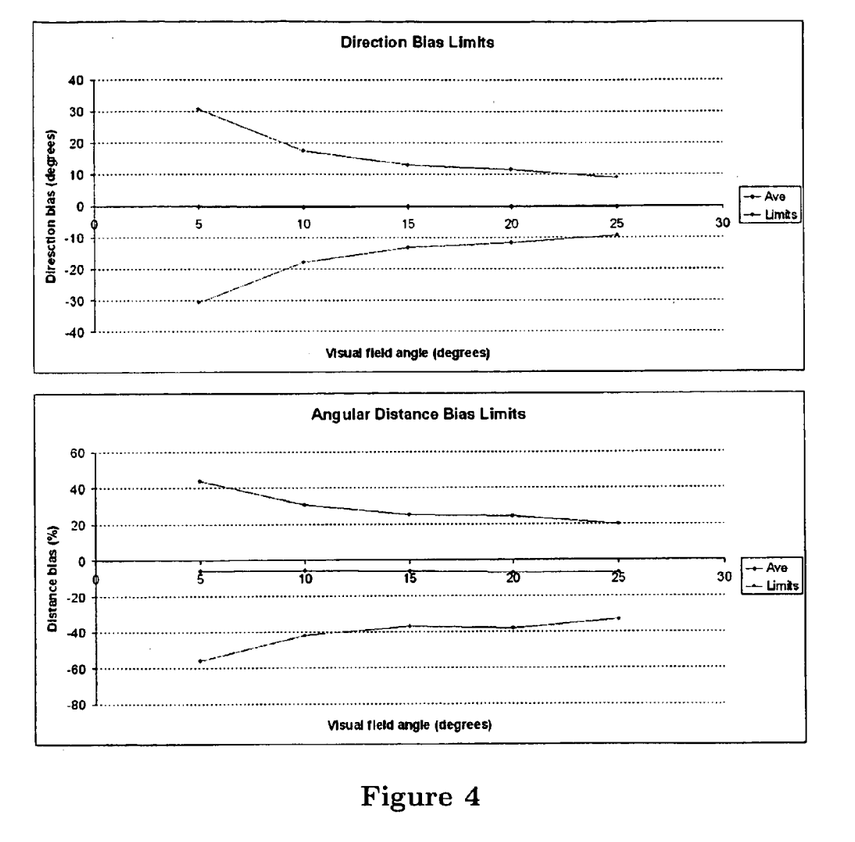
FIG. 4(a) is a plot of direction bias limits as a function of visual field angle.
FIG. 4(b) is a plot of angular distance bias limits as a function of visual field angle.

In practice, there is a natural variation in the difference between the vector change in fixation point and the vector change in the screen position of the stimuli, even when a fixation change does relate to the stimulus displayed. Hence, it is important to know how much variation is acceptable before a stimulus is classed as being 'unseen'. To deal with this, parameters used within the algorithm designed to make this decision are based on data collected from many subjects and are dependant upon the size of visual field angle being assessed. Examples of the limits for the difference in direction and angular length of the two vectors being compared are shown in FIG. 4.

Figure 5:
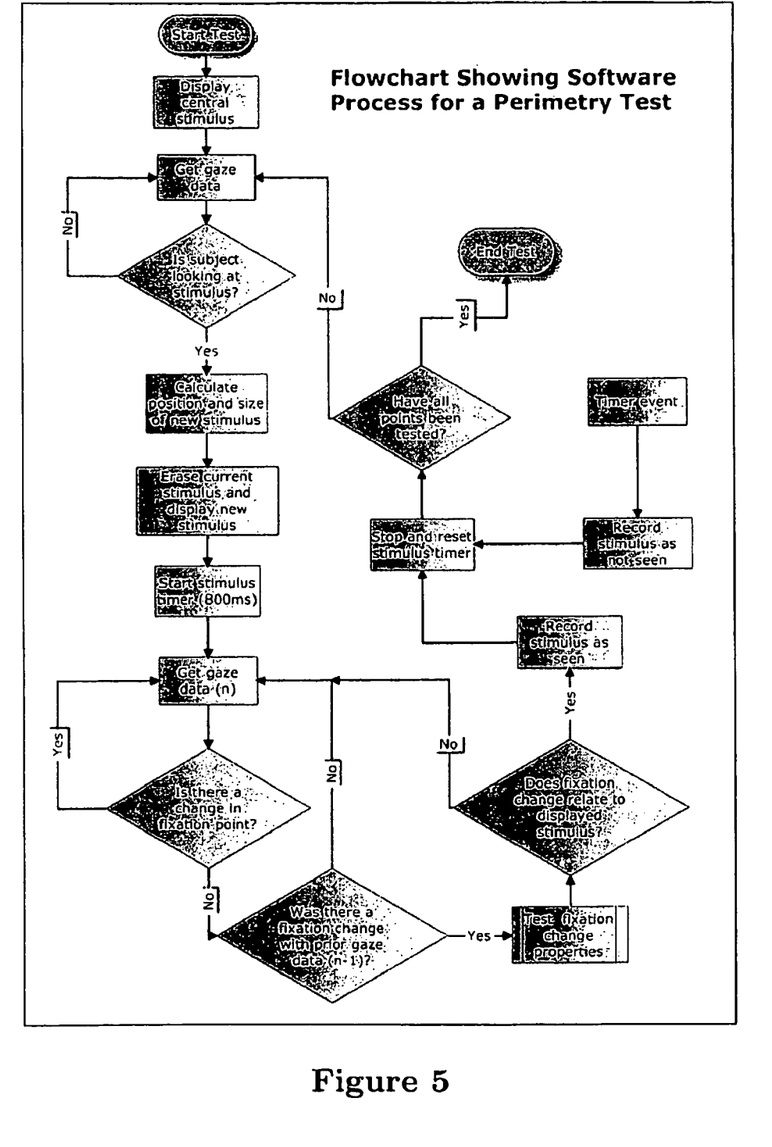
FIG. 5 is a flow diagram of a process for testing perimetry.

FIG. 5 shows the steps in a method for testing visual fields. In practice, this method is implemented using a computer program running on the processor/personal computer. Typically, each of the patient's eyes is measured separately and the results averaged, although this is not essential. At the start of the test, a stimulus 14 is displayed in the centre of the screen 12 to cause the patient to fixate on a central point. When the stimulus 14 is displayed the eye tracker 16 captures eye gaze data in order to verify whether the patient is indeed gazing at the stimulus 14. In the event that the gaze data suggests that the patient is not fixating on the correct point, further gaze data is captured. This is repeated until the system is confident that the patient is looking at the central stimulus 14. Animations to attract attention can be used if required.

After the system determines that the patient is fixating on the first, central stimulus, the position and size of the next stimulus are calculated. The position of the next stimulus is calculated using the distance from the current fixation point (in this case the central stimulus) to the subject's eyes, as measured in real time using the eye tracker, and the points in the subject's visual field that are to be assessed. As illustrated in FIG. 2, the on-screen position can vary depending on the measured distance of the patient from the fixation point. For a particular examination there are a number of different visual field points to be assessed. Generally, the order in which the selected points are assessed is random. Once the next stimulus position is determined, the current stimulus is erased and the next stimulus displayed in the new position. A timer is started when the stimulus is displayed. The timer runs in the background and acts as a countdown. If the displayed stimulus is not detected as 'Seen' within this time then the stimulus is categorised as 'Not Seen'. Typically, this time is set to a pre-determined limit, for example 1 second.

Next, gaze data is captured. For the Tobii tracker this is done every 20 ms or so. The captured data is used to determine whether there has been a change in the fixation point. If there has, the following gaze data point is used to determine whether there has been a further change in the fixation point, this continues until no change is found. In this manner the movement of the user's eye towards an end, fixation point can be found. If there is no change in fixation with a gaze data point and the prior gaze data point did indicate a change in fixation then this indicates the end of the subject's fixation change. Once a change is detected the fixation change properties are tested to identify whether the current fixation change corresponds to the location of the new stimulus.

Figure 6:
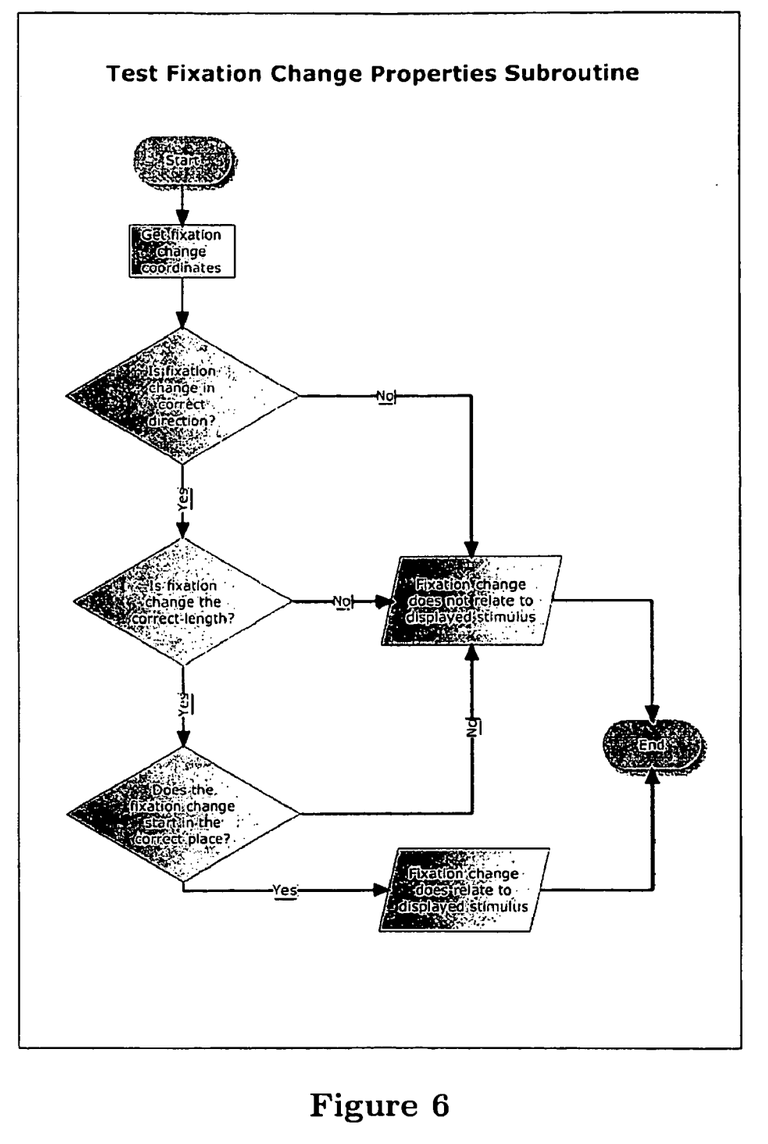
FIG. 6 is flow diagram of a sub-routine for a fixation change properties test.

FIG. 6 illustrates steps for testing the fixation change properties. Firstly, the fixation change properties are used to identify whether the direction of the change of the fixation is correct when compared with a vector from the first stimulus to the new stimulus. If not, then the fixation is determined not to relate to the new stimulus and the system returns to the capture gaze data step of FIG. 5. If yes, then the fixation data and three-dimensional eye position data is used to determine the angular distance between the first fixation point and the second fixation point. If this distance differs from the known angular separation between the first stimulus and the second stimulus, then the fixation is determined not to relate to the new stimulus and the system returns to the capture gaze data step of FIG. 5. In contrast, if the angular distance does correspond to the separation of the first stimulus and the second stimulus then it is concluded that the fixation does relate to the displayed stimulus.

Returning to FIG. 5, in the event that the next stimulus is identified as having been seen, this event is recorded. The stimulus timer is then stopped and reset. If not all points have been tested then the test is run again with a new visual field point. Otherwise, the test is completed.

Using data captured in accordance with the invention, it is possible to perform ASP without needing the patient to be in a fixed position. For children, this is a very significant technical advantage. The system could also be used to assess a person's reaction to peripheral stimuli within a recreated "real-world" environment such as street or home scene or driving situation. This can be helpful as their reactions can be affected by different disease states.

In the method described above the visual field position to be tested is selected and the position of the stimulus on the display calculated as a function of the patient's three-dimensional eye position. In an alternative embodiment, the stimulus may be positioned at one of a plurality of selected positions on the display and then the visual field position associated with this position calculated using the three dimensional position of the patient's eye(s).

The peripheral stimulus presented will generally be of the same type for all subjects, for example a circle or disc. To keep the test interesting for children, however, the visual field stimulus can be changed to interesting audio-visual animations appropriate to their developmental age once the original peripheral stimulus has been detected as 'seen'. For instance, the human face is a potent visual fixation stimulus for an infant and cartoon figures can be used for young children. This will motivate the children to submit to the test and increase compliance rate without changing the properties of the required visual field stimulus. The test can also be interrupted anytime by sounds or video to draw the attention of a distracted child back to the screen.

The method in which the invention is embodied does not require any cooperation or understanding from a child. Also, the child is not required to learn any task or to give any subjective response. This removes the need for vigilance, and endurance or understanding of the test method on the part of the child. Moreover, the absence of subjective responses from the child also eliminates false-positive and false-negative errors, which increases the reliability of the test. Also, the child's head movement is not restricted in any way and the system does not require any form of physical contact with the child, which makes it more comfortable. A further advantage is that a continuous fixation on a stationary central fixation target is not needed.

As well as measuring visual fields, the system of FIG. 1 can be used for numerous other eye tests, for example visual acuity, colour vision, contrast sensitivity and colour-contrast sensitivity, in both children and adults. Visual acuity is the ability to discriminate two stimuli separated in space whilst colour vision is the ability to differentiate two different colours. Contrast sensitivity is the ability to discriminate the difference between shades of grey or hues of colour.

Conventional methods used for children depend upon a skilled orthoptist observing the child's direction of gaze while presenting the child with picture cards. The technique used is called 'preferential looking'. The picture cards are designed so that a picture is located either in the top half or bottom half of the card. The picture design is that of the vanishing optotype because the pictures seem to disappear from the perspective of the child, when at their resolution limit. If the child's visual acuity is good enough the picture is visible and they will orientate their gaze in the direction of the picture, otherwise the picture is merged with the background and seems invisible to the child, in this situation the picture cannot be seen and so the child cannot look at the picture. A problem with conventional techniques is that they rely on a skilled orthoptist observing the child's direction of gaze. This can make it difficult to accurately detect the change of direction.

Eye tracking has the potential to more accurately and reliably detect change of direction of gaze towards a test target. Using the arrangement of FIG. 1, this could be done by presenting vanishing optotype targets and using the eye tracker to detect if the subject looks at a picture. Alternatively stationary pictures with varying levels of visual acuity and contrast sensitivity could be presented on the screen. Likewise, different colour images could be presented, so as to test colour vision deficiency. In any case, the pictures are presented somewhere away from the subject's gaze point and eye movement is tracked. If the subject looks at the picture then it can be concluded that they were able to see it, and if they did not look at the picture then they were not able to see it. The test proceeds based on the subject's responses, i.e. if a picture is seen then the next picture that is shown is at a more difficult level of acuity or contrast sensitivity or of a different colour vision deficiency test. This is repeated until the subject's visual acuity or contrast sensitivity level is reached, or specific colour vision deficiency tests have been carried out. In this case, the software for controlling the test is similar to that used for visual field assessment, although it is simpler, as it is only required to recognise that the subject looks at the picture rather than assessing fixation change properties from one point to another.

A skilled person will appreciate that variations of the disclosed arrangements are possible without departing from the invention. For example, although the invention has been described for use in testing visual fields in children, it will be appreciated that it could also be used for those with learning difficulties and the elderly. In addition, although the invention is described primarily with reference to a conventional flat screen monitor, other screens, for example curved screens could be used. This could extend the vision test range. Accordingly the above description of the specific embodiment is made by way of example only and not for the purposes of limitation. It will be clear to the skilled person that minor modifications may be made without significant changes to the operation described.

The invention claimed is:

1. A system for testing visual fields comprising:
a display for presenting a visual stimulus;
an eye tracker for tracking movement of at least one of a patient's eyes to determine its position in three dimensions without requiring the patient to wear any tracking equipment;
means for changing the position of the stimulus on the display by an amount that is a function of the tracked three dimensional position of the patient's eye and a visual field position that is to be tested, and
means for using the change to the position of the stimulus and any tracked eye movement to assess the patient's visual field.

2. A system as claimed in claim 1 further comprising means for varying the size of the stimulus presented, as a function of three dimensional position of the patient's eye and a visual field position that is to be tested, so that the stimulus is of a constant angular diameter throughout the test.

3. A system as claimed in claim 1 further comprising means for varying the shape of the stimulus presented, as a function of three-dimensional position of the patient's eye relative to the display and the visual field position that is being tested, so that the stimulus is presented at a constant angular shape.

4. A system as claimed in claim 1 adapted to present a first stimulus;
capture gaze data for that first stimulus; present a second stimulus, and test whether the patient is gazing at that second stimulus.

5. A system as claimed in claim 4 wherein testing whether a patient has seen the second stimulus involves determining a direction in which the patient's eye(s) moved after the second stimulus is present and comparing this direction with the vector direction associated with a line between the first stimulus and the second stimulus.

6. A system as claimed in claim 4 wherein testing whether a patient has seen the second stimulus involves determining the angular distance between a first fixation point and a second fixation point and comparing this with the angular distance between the first and second stimuli.

7. A system as claimed in claim 1 the system being further operable to measure at least one of visual acuity, colour vision, contrast sensitivity and colour-contrast sensitivity.

8. A system as claimed in claim 1 wherein the display is curved.

9. A system as claimed in claim 1 wherein the eye tracker has a head position tolerance of more than 10 cm×10 cm×10 cm (Horizontal×Vertical×Distance from the tracker).

10. A system as claimed in claim 9 wherein the eye tracker has a head position tolerance of more than 20 cm×10 cm×20 cm.

11. A method for testing vision comprising:
presenting a visual stimulus on a screen;
tracking movement of at least one of a patient's eyes using an eye tracker to determine a gaze point and its position in three dimensions without requiring the patient to wear any tracking equipment;
changing the position of the stimulus on the display by an amount that is a function of the tracked three dimensional position of the patient's eye and a visual field position that is to be tested, and
using the change to the position of the stimulus and any tracked eye movement in response to the change of the position to assess the patient's visual field.

12. A non-transitory computer readable storage medium comprising code or instructions for presenting a visual stimulus on a display; receiving data from an eye tracker on the three dimensional position of a patient's eye(s); changing the position of the stimulus on the display by an amount that is a function of the tracked three dimensional position of the patient's eye and a visual field position that is to be tested, and using the change to the position of the stimulus and any tracked eye movement in response to the change of the position to assess the patient's visual field.

13. A non-transitory computer readable storage medium as claimed in claim 12 that is configured to vary the size of the stimulus presented, as a function of three dimensional position of the patient's eye and a visual field position that is to be tested, so that the stimulus is of a constant angular size throughout the test.

14. A non-transitory computer readable storage medium as claimed in claim 12 that is adapted to relocate the position of the stimulus on the screen and use eye-tracking information to determine whether the patient is looking at the stimulus at its new position.

15. A non-transitory computer readable storage medium as claimed in claim 12 that is adapted to present a first stimulus; capture gaze data for that first stimulus; present a second stimulus, and test whether the patient has seen that second stimulus.

16. A non-transitory computer readable storage medium as claimed in claim 15 wherein determining whether a patient has seen the second stimulus involves using eye tracking information to determine a direction in which the patient's eye(s) moved and compare this with the vector direction associated with a line between the first stimulus and the second stimulus.

17. A non-transitory computer readable storage medium as claimed in claim 15 wherein testing whether a patient has seen the second stimulus involves determining the angular distance between a first fixation point and a second fixation point and comparing this with the angular distance between the first and second stimuli.

18. A non-transitory computer readable storage medium as claimed in claim 12 that is arranged to determine a time between showing a first stimulus, deleting that stimulus and displaying a second stimulus and the time for a patient to respond to the change in stimulus.

19. A non-transitory computer readable storage medium as claimed in claim 18 wherein the code or instructions are adapted to determine whether the patient has seen the stimulus at its new position by comparing the direction of the change of the fixation and the direction of a vector from the first stimulus to the new stimulus and the angular distance between the first fixation point and the second fixation point and the angular separation between the first stimulus and the second stimulus.

20. A non-transitory computer readable storage medium as claimed in claim 12 that is arranged to determine a time between showing a first stimulus, deleting that stimulus and displaying a second stimulus and the time for a patient to respond to the change in stimulus and use this to identify, at least in part, whether the patient is responding to the stimulus.

21. A system for testing visual fields comprising:
a display for presenting a visual stimulus;
an eye tracker for tracking movement of at least one of a patient's eyes to determine its position in three dimensions without requiring the patient to wear any tracking equipment;
means for changing the position of the stimulus on the display;
means for determining the visual field position associated with the new position of the stimulus using its position on the display and the three dimensional position of the patient's eye(s), and
means for using the change to the position of the stimulus, and any tracked eye movement in response to the change of the position to assess the patient's visual field.

22. A system for testing vision comprising a display for presenting a visual stimulus; means for causing a change to the stimulus; an eye tracker for tracking movement of a patient's eye and means for using the change to the stimulus and any corresponding tracked eye movement to assess the patient's vision, wherein the means for causing a change to the visual stimulus are operable to vary separately or simultaneously two or more of the position of the stimulus; the colour of the stimulus; the contrast of the stimulus.

23. A system as claimed in claim 22 wherein two stimuli are presented and the means for causing a change are operable to vary the separation of the two stimuli.

24. A non-transitory computer readable storage medium comprising code or instructions for presenting a visual stimulus on a screen; causing a change to the stimulus; using the change to the stimulus and any corresponding tracked eye movement to assess a patient's vision, wherein the code or instructions for causing a change to the visual stimulus are adapted to vary separately or simultaneously two or more of the position of the stimulus; the colour of the stimulus; the contrast of the stimulus relative either to a background or another stimulus.

* * * * *